US005366696A

United States Patent [19]

Williams

[11] Patent Number: 5,366,696

[45] Date of Patent: Nov. 22, 1994

[54] OXYGENATION APPARATUS FOR OXYGENATING A CARRIER LIQUID BY SPRAYING

[75] Inventor: Michael R. Williams, Burlington, Canada

[73] Assignee: 1077075 Ontario Inc., Oakville, Canada

[21] Appl. No.: 1,630

[22] Filed: Jan. 7, 1993

[51] Int. Cl.[5] .............................................. A61M 11/00

[52] U.S. Cl. ........................................ 422/45; 422/47; 435/2; 128/DIG. 3; 239/346

[58] Field of Search ..................... 422/45, 47, 49, 110, 422/44, 46; 435/2; 128/DIG 2, 200.14, 200.18, 200.19, 200.20, 200.21, 200.23; 239/346, 338, 432

[56] References Cited

U.S. PATENT DOCUMENTS

| | | | |
|---|---|---|---|
| 2,827,901 | 3/1958 | Jones | 422/45 |
| 3,097,645 | 7/1963 | Lester | 239/338 |
| 3,104,062 | 9/1963 | Mahon | 239/346 |
| 3,584,792 | 6/1971 | Johnson | 239/338 |

*Primary Examiner*—Lyle A. Alexander
*Attorney, Agent, or Firm*—Bereskin & Parr

[57] ABSTRACT

An oxygenation apparatus for introducing a flow of oxygen gas molecules into a carrier liquid in a one-pass operation comprises a receiving chamber for receiving carrier liquid, a contacting chamber for allowing the oxygen gas molecules to thoroughly contact the carrier liquid, and a separating partition located between the receiving chamber and the contacting chamber so as to preclude the return of oxygenated carrier liquid from the contacting chamber to the receiving chamber. There is an inlet for introducing oxygen gas molecules at a pressure slightly above the ambient surrounding air pressure into the apparatus, which terminates in an end portion having a gas introduction orifice. The gas introduction orifice is located in fluid communication with the receiving chamber, and causes a jet of oxygen gas molecules to be emitted therefrom. There is a spray orifice located in the separating partition, positioned to allow carrier liquid to be sprayed into the contacting chamber by the jet of oxygen gas molecules. A passageway has is located so the carrier liquid can pass from the receiving chamber to the space between the gas introduction orifice and the spray orifice, allowing oxygenated carrier liquid to exit from the contacting chamber. The oxygen gas includes molecules in the diatomic form ($O_2$), and molecules in at least one of either the triatomic form ($O_3$) and the monatomic form ($^1O_2$). When the oxygen gas molecules are introduced into the apparatus, they force the carrier liquid in the space between the gas introduction orifice and the spray orifice to be sprayed through the spray orifice into the contacting chamber so that no bubbles are formed.

11 Claims, 2 Drawing Sheets

OXYGENATION APPARATUS FOR OXYGENATING A CARRIER LIQUID BY SPRAYING

FIELD OF THE INVENTION

This invention relates to apparatus for introducing oxygen gas molecules into a carrier liquid, and more particularly introducing oxygen gas molecules into blood or other suitable carrying liquid for subsequent injection into a human blood stream.

BACKGROUND OF THE INVENTION

Oxygen is an allotropic element, with the most common form of the gas being the di-atomic form ($O_2$). Ozone ($O_3$) and singlet oxygen ($^1O_2$) are other forms of the gas that occur naturally and that can be created artificially. Ozone is the triatomic form of oxygen and is relatively unstable. One method of creating ozone is to expose $O_2$ gas (pure medical oxygen) to laser light having a wave length of about 180 to 187 nm. Other methods of forming ozone are well known. Singlet oxygen is the monatomic form of oxygen and is highly unstable. One method of creating singlet oxygen is to expose ozone to ultra-violet light of a wavelength of 253.7 nm. It is also known to expose a mixture of oxygen gas containing ozone and singlet oxygen to visible light of a wavelength of between about 500 and 800 nm to further induce the formation of singlet oxygen. Other methods of forming singlet oxygen are well known.

The benefits of ozone gas molecules ($O_3$) and singlet oxygen gas molecules ($^1O_2$) are well known in the medical community for treatment of blood and human tissue in order to fight disease or other pathogens, or at least to ameliorate the effects thereof. Many diseases have been shown to be positively effected through the administration of ozone and singlet oxygen. Ozone has been found to kill cancer cells, to be effective against various viruses and fungi, and to inactivate a wide variety of bacteria including Pseudomonas Aeruginosa, Staphylococcus Aureus and Mycobacterium Tuberculosis. Ozone has also been found to have disruptive effects on malignant tumour cells. The administration of ozone is also known to have beneficial effects to a person's health in general by way of stimulating oxygen metabolism. Studies of the effects of singlet oxygen indicate similar or even more dramatic effects. It has also been shown that the administration of ozone and singlet oxygen to a healthy person, through direct inhalation, can help prevent various diseases, such as those discussed above.

One very important use of ozone and singlet oxygen is in the sterilization treatment of blood for blood that is being removed from a donor and administered to a recipient. Through the use of ozone and singlet oxygen, it is possible to deactivate a variety of potential viral contaminants of blood, including HIV-1 and Hepatitis.

It is known to introduce ozone and singlet oxygen directly to diseased tissue. Alternatively, the ozone and singlet oxygen may first be introduced to a carrier liquid such as USP water or blood, and then the carrier liquid may be introduced to the diseased tissue or injected into a person's bloodstream, as appropriate. In order to treat a person having a given disease, an alequot of blood is drawn from the person, the alequot is treated, and is then injected back into the person. Units of blood used for transfusion are each separately treated and subsequently used as necessary.

The introduction of ozone and singlet oxygen gas molecules to a person's blood, or even to USP water, is a problematic process. It is desirable to have the gas molecules introduced as quickly as possible to the carrier liquid in order to minimize time and expense. However, quick introduction of these gas molecules through the use of prior art technology can readily cause a formation of bubbles, which is undesirable, and also can lead to haemolysis—the destruction of the cell walls of the red blood cells and the subsequent loss of haemoglobin therefrom.

What is not known is how to properly and effectively introduce required quantities of ozone or singlet oxygen into a liquid carrier in an efficient manner, so that a reasonably high volume alequot of blood can be treated in a relatively short period of time, with causing bubbling and potentially causing haemolysis of blood.

DESCRIPTION OF THE DRAWINGS

Embodiments of the present invention will now be described by way of the accompanying drawings, in which.

PRIOR ART

Figure 1:
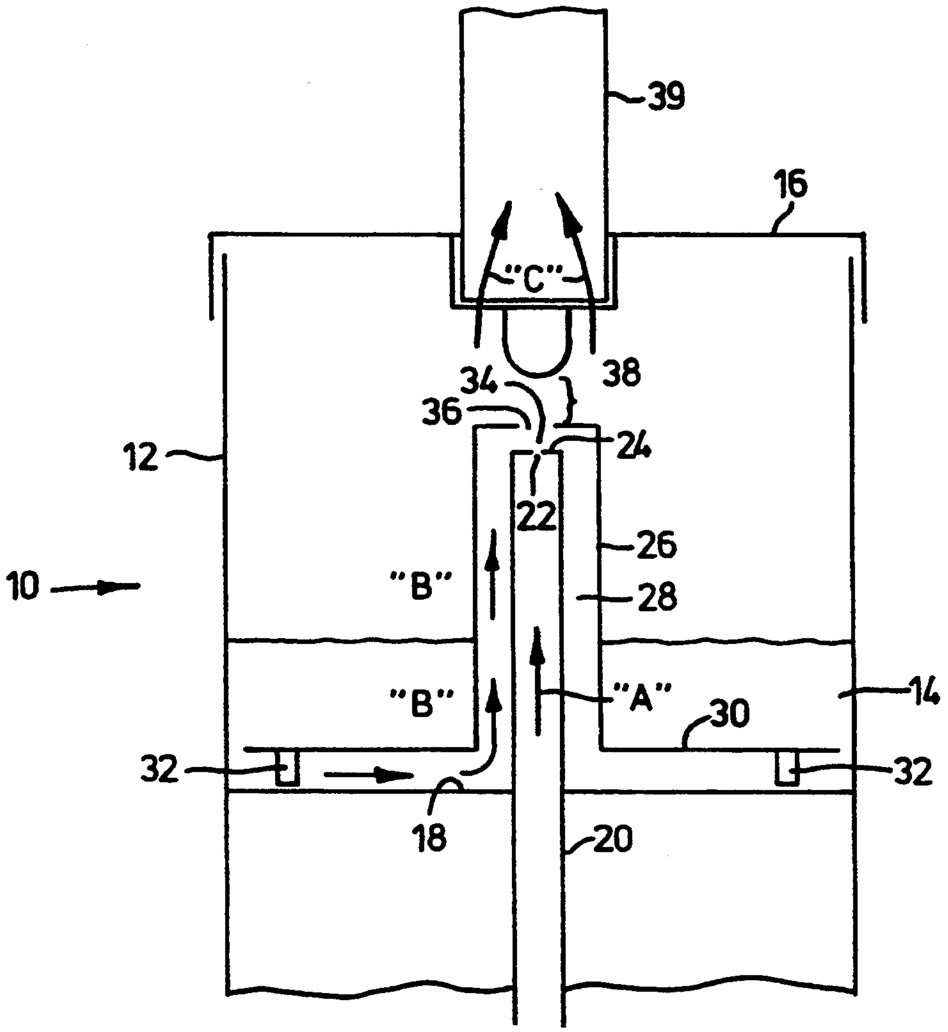
FIG. 1 is a pictorial cross-sectional view of a prior art nebulizer.
Figure 2:
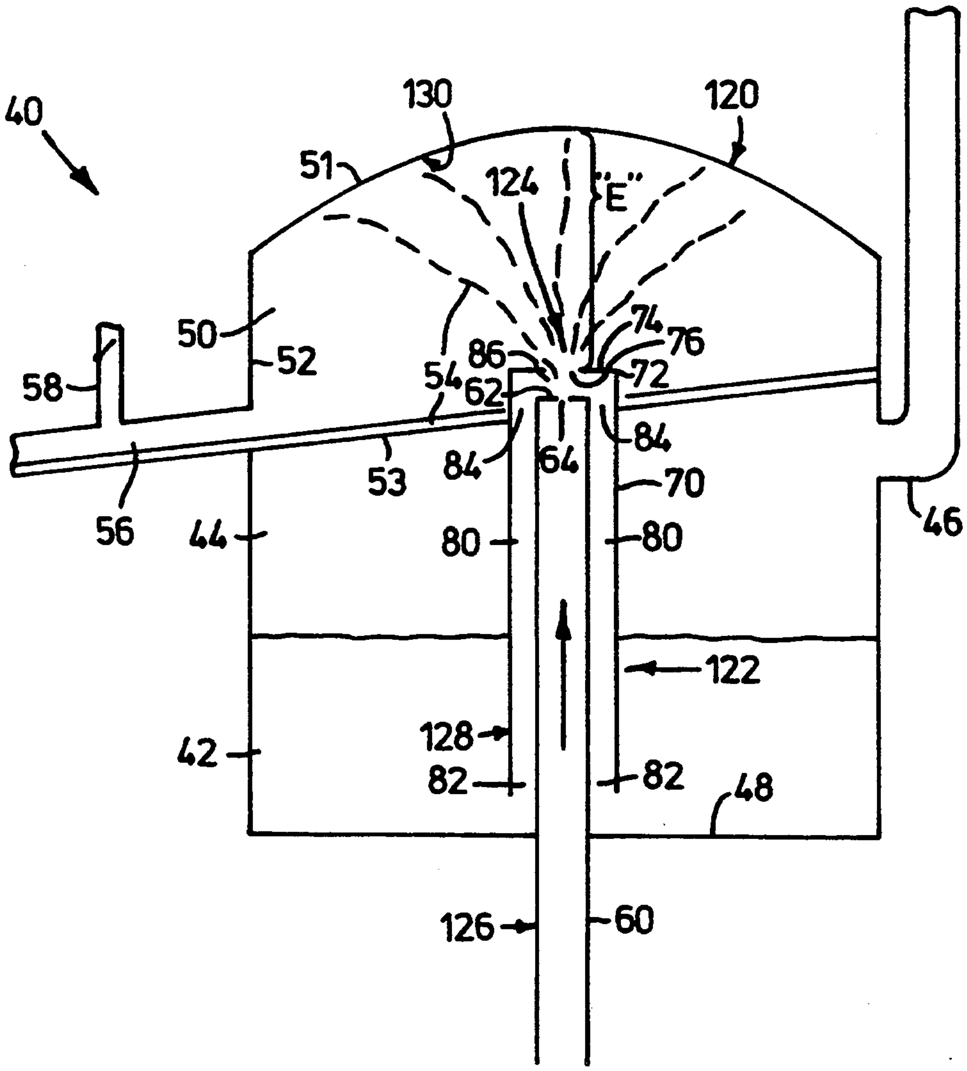
FIG. 2 is a pictorial cross-sectional view of the oxygenation apparatus of the present invention.

The closest known prior art is a nebulizer for use in conjunction with an inhaler that is used with certain types of medicine to be inhaled into the lungs, such as would be required by an asthmatic person. This prior art nebulizer is shown in FIG. 1, with the nebulizer 10 comprising main chamber 12 that is adapted to hold a quantity of liquid medicine 14. The main chamber 12 is closed off by a cap member 16. At the opposite end thereof there is a floor 18 with an oxygen inlet 20 extending therethrough, and that is adapted to allow for the flow of oxygen into the main chamber 12 as shown by arrow "A". The oxygen inlet 20 has a gas introduction orifice 22 in the end portion 24 thereof. A removable channelling member 26 is located within the main chamber 12, and defines an annular passageway 28 for the liquid medicine 14 to reach the gas introduction orifice 22 as shown by arrows "B". The horizontally oriented base portion 30 of the channelling member 26 has a plurality of small feet 32 depending therefrom, which feet 32 raise the level of the base portion 30 above the floor 18 of the main chamber 12, so as to allow the liquid medicine 14 to reach the annular passageway 28.

When the oxygen gas molecules flow through the oxygen inlet 20 and then through the gas introduction orifice 22, a low pressure area is created in the area around the space 34 between the nebulizing orifice 36 and the gas introduction orifice, which causes the liquid medicine 14 to be drawn up the annular passageway 28, to the space 34. The oxygen flow impacts the liquid medicine that reaches this space 34 and sprays it through the nebulizing orifice 36 so as to impact on the impact member 38, so as to thereby nebulize the liquid medicine 14. The flow of nebulized oxygen gas continues through the outlet 39 as shown by arrows "C". Any of the liquid medicine 14 that is not carried by this flow of oxygen drops back down into the liquid medicine 14. This process continues until all of the liquid medicine 14 is nebulized into a fine mist and carried by the oxygen flow through the outlet 39.

This prior art arrangement can be used to import a relatively high concentration of oxygen gas molecules, such as ozone, into a carrier liquid. Such a relatively high concentration of oxygen gas molecules would be used when introducing ozone into a patient's blood stream for the purpose of treating disease. For this purpose, only a small alequot of blood is required—perhaps 5 cc's to 10 cc's—or even less. The blood is recirculated through the nebulizer several times until the desired level of oxygen concentration is realized. Preferably, the rate of flow of ozone would be about 0.75 l/min., which is significantly lower than the flow of oxygen used to nebulize liquid medicine, so as to not cause damage to the red blood cells.

In order to oxygenate blood for the purpose of blood purification, a lower concentration of oxygen gas molecules is required. However, a much greater volume of blood—typically about one liter—is to be purified. The prior art nebulizer would need to be re-filled with blood perhaps 100 to 200 times in order to process a full liter. This would take a considerable period of time, which is highly undesirable. Further, it has been found that the use of a nebulizer introduces a greater concentration of oxygen gas molecules than is necessary for blood purification, because of the misting that occurs after the impact of the blood on the impact member 38. Resultingly, the flow rate of the oxygen gas molecules must be reduced a significant amount, which would further increase the amount of time taken to purify a liter of blood. The use of a larger nebulizer would not solve the above discussed problems because it would be necessary to increase the gas flow to an unacceptably high rate, thus causing unwanted increased introduction of oxygen molecules into the blood and also possibly causing damage to the red blood cells.

A further characteristic of this prior art device is that it tends to form foaming or bubbling of certain liquids, especially if the carrier liquid is blood. Such foaming and bubbling is unacceptable for oxygenating a carrier liquid, especially if the carrier liquid is blood. This is largely due to the fact that the distance between the impact member 38 and the nebulizing orifice 36, as indicated by the bracket "D", is quite small. Thus, the liquid medicine being carried by the flow of oxygen impacts quite strongly on the impact member 38, so as to cause foaming and bubbling. Further, such high impact can readily cause damage to the cell walls of the red blood cells.

SUMMARY OF THE INVENTION

An oxygenation apparatus for introducing a flow of oxygen gas molecules into a carrier liquid in a one-pass operation, is disclosed. The apparatus comprises a receiving chamber for receiving the carrier liquid therein, with a carrier liquid inlet for introducing the carrier liquid to be oxygenated into the receiving chamber, and a contacting chamber for allowing the oxygen gas molecules to thoroughly contact the carrier liquid. There is a separating partition located between the receiving chamber and the contacting chamber, the separating partition being adapted to substantially physically separate the receiving chamber and the contacting chamber from each other so as to preclude the return of oxygenated carrier liquid from the contacting chamber to the receiving chamber. The oxygenation apparatus also has an oxygen gas inlet for introducing the oxygen gas molecules at a gas pressure slightly above the ambient surrounding air pressure into the apparatus. The oxygen gas inlet terminates in an end portion having a gas introduction orifice therein, with the gas introduction orifice located in fluid communication with the receiving chamber. The gas introduction orifice is further adapted to cause a jet of oxygen gas molecules to be emitted therefrom. A spray orifice is located in the separating partition, and is positioned and adapted to allow carrier liquid to be sprayed therethrough into the contacting chamber by the jet of oxygen gas molecules from the gas introduction orifice. A passageway having a first end and a second end, connects at the first end thereof the receiving chamber in fluid communication with the space between the gas introduction orifice and the spray orifice at the second end thereof, such that the carrier liquid can pass from the receiving chamber the space between the gas introduction orifice and the spray orifice. An oxygenated carrier liquid outlet allows the oxygenated carrier liquid to exit from the contacting chamber. The oxygen gas molecules include molecules in the diatomic form ($O_2$), and molecules in at least one of either the triatomic form ($O_3$) and the monatomic form ($^1O_2$). The oxygen gas molecules are introduced into the apparatus through the oxygen gas inlet, so that the oxygen gas molecules exit the oxygen gas inlet through the gas introduction orifice so as to force the carrier liquid that is located in the space between the gas introduction orifice and the spray orifice to be sprayed through the spray orifice into the contacting chamber such that no bubbles are formed by the spray, thus causing the oxygen gas molecules to thoroughly contact the carrier liquid so as to thereby oxygenate the carrier liquid.

DESCRIPTION OF THE PREFERRED EMBODIMENT

Reference will now be made to FIG. 1, which shows the oxygenation apparatus 40 of the present invention in use. The oxygenation apparatus 40 is used to introduce a flow of oxygen gas molecules into a carrier liquid 42 in a one-pass operation. This basically means that the oxygen gas molecules are introduced to each portion of the carrier liquid 42 once, and that portion of the carrier liquid 42 that has thereby been oxygenated is then removed from the oxygenation apparatus 40 and collected for subsequent medical use. The oxygen gas molecules include molecules in the diatomic form ($O_2$) and molecules in at least one of either the triatomic form ($O_3$) and the monatomic form ($^1O_2$).

The oxygenation apparatus 40 comprises a receiving chamber 44 for receiving the carrier liquid 42 therein and a carrier liquid inlet 46 for introducing the carrier liquid 42 to be oxygenated into the receiving chamber 44. The carrier liquid 42 can be introduced through the carrier liquid inlet 46 on a continuous basis or in discrete amounts. The carrier liquid 42 collects in the bottom 48 of the receiving chamber 44.

Above the receiving chamber 44 is a contacting chamber 50 that allows for oxygen gas molecules to thoroughly contact the carrier liquid 42, in a manner that will be described in greater detail subsequently. The contacting chamber 50 has a generally concave top portion 51 that is thereby adapted to receive a spray of carrier liquid 42, as will be described subsequently.

There is a separating partition 53 located between the receiving chamber 44 and the contacting chamber 50. The separating partition 53 is adapted to substantially physically separate the receiving chamber 44 and the contacting chamber from each other. In this manner, oxygenated carrier liquid 54 in the contacting chamber 50 is precluded from returning to the receiving chamber 44, thereby allowing the oxygenation apparatus 40 of the present invention to provide a one-pass type operation. The separating partition 53 preferably slopes downwardly to allow the oxygenated carrier liquid 54 to flow therealong to an oxygenated carrier liquid outlet 56 that allows the oxygenated carrier liquid 54 to exit from the contacting chamber 50. The oxygenated carrier liquid outlet 56 is attached to a standard receptacle (not shown) of a type that is suitable for collecting the oxygenated carrier liquid 54. Extending upwardly from a top portion of the oxygenated carrier liquid outlet 56 is a one-way oxygen gas vent 58 for allowing any of the oxygen gas molecules that have passed into the contacting chamber 50 to vent to the ambient surroundings.

At the bottom 48 of the receiving chamber 44 is an oxygen gas inlet 60 for introducing oxygen gas molecules into the oxygenation apparatus 40. The oxygen gas molecules are introduced at a gas pressure slightly above the ambient surrounding air pressure—typically in the order of a few inches of $H_2O$ gauge pressure—so as to cause a flow of the oxygen gas molecules from the oxygen gas inlet 60 into the contacting chamber 50 and then out of the contacting chamber 50 through the oxygenated carrier liquid outlet 56. The gas pressure within the contacting chamber 50 is at a level between the gas pressure within the oxygen gas inlet 60 and the gas pressure of the ambient surroundings. The end portion 62 of the oxygen gas inlet 60 has a gas introduction orifice 64 therein, which is fairly small in diameter—perhaps about 0.5 mm—and is thereby adapted to cause a jet of oxygen gas molecules to be emitted therefrom.

An annular wall member 70 extends downwardly from the separating partition 53 to within a small distance—perhaps about 1.0 mm or even less—from the bottom 48 of the receiving chamber 44. Preferably, the separating partition 53 is extended upwardly at the annular wall member 70 so as to allow the top end 72 of the annular wall member 70 to be generally above the level of the rest of the separating partition 53. The top end 72 of the annular wall member 70 terminates in a flow restricting portion 74 that has a spray orifice 76 centrally located therein. The spray orifice 76 is preferably about 1.0 mm in diameter. In any event, the spray orifice 76 should be larger in diameter than the gas introduction orifice 64 so as to allow all of the gas emitted from the gas introduction orifice 64 to pass through the spray orifice 76 without impinging on the flow restricting portion 74.

The annular wall member 70 encircles and substantially covers the oxygen gas inlet 60 and defines a passageway 80 around the oxygen gas inlet 60. The passageway 80 is oriented so as to extend substantially vertically upwardly and has a first end 82 located at the bottom thereof and a second end 84 located at the top thereof. The passageway 80 connects at the first end 82 thereof to the receiving chamber 44 in fluid communication with the space 86 that is located between the gas introduction orifice 64 and the spray orifice 76 at the second end 84 thereof.

In use, oxygen gas molecules are fed into the oxygen gas inlet 60 at a pressure that is slightly above ambient pressure. It is important to use a gas pressure that is only slightly above ambient air pressure, which therefore keeps the rate of flow of oxygen gas molecules quite low, so as to preclude any foaming or bubbling of the carrier liquid 42, or in the event that the carrier liquid 42 is blood, to preclude any damage to the haemoglobin cell walls. The flow of oxygen gas molecules exits the oxygen gas inlet 60 through the gas introduction orifice 64 as a jet of oxygen gas molecules. This jet of oxygen gas molecules causes a low gas pressure area between the gas introduction orifice 64 and the spray orifice 76, which in turn draws the carrier liquid 42 in the receiving chamber 44 up the passageway 80 until it reaches the space 86. Once the carrier liquid 42 reaches this space 86, it is impacted by the jet of oxygen gas molecules exiting the gas oxygen inlet through the gas introduction orifice 64. The carrier liquid 42 is thereby sprayed through the spray orifice 76 into the separating partition 53. Resultingly, the oxygen gas molecules thoroughly contact the carrier liquid 42 so as to thereby oxygenate the carrier liquid 42.

The spray of oxygen gas molecules and carrier liquid 42 typically impacts on the generally concave top portion 51 of the contacting chamber 50, so as to cause increased contact of the oxygen gas molecules and the carrier liquid 42. The top portion 51 is preferably at a distance "E" from the spray orifice 76 that is sufficient to cause the spray of carrier liquid 42 from the spray orifice 76 to slow down considerably so as to significantly reduce the impact of the carrier liquid 42 on the top portion 51. The carrier liquid 42 then either drips off the top portion 51 of the contacting chamber 50 or flows down the inner walls 52 of the contacting chamber 50, and collects on the separating partition 53. The spray orifice 76 is located substantially above the level of the rest of the separating partition 53 so as to maintain any volume of oxygenated carrier liquid 54 on the separating partition 53 below the level of said spray orifice 76, and thereby preclude any oxygenated carrier liquid 54 from entering the spray orifice 76 and subsequently mixing with the untreated carrier liquid 42 therebelow.

Other modifications and alterations may be used in the design and manufacture of the oxygenation apparatus of the present invention without departing from the spirit and scope of the accompanying claims.

What is claimed is:

1. An oxygenation apparatus for introducing a flow of oxygen gas molecules into a carrier liquid in a onepas operation, said apparatus comprising:
 - a receiving chamber for receiving said carrier liquid therein;
 - a carrier liquid inlet for introducing said carrier liquid to be oxygenated into said receiving chamber;
 - a contacting chamber in fluid communication with said spray orifice for allowing said carrier liquid;
 - a separating partition located between said receiving chamber and said contacting chamber, said separating partition constructed and adapted to substantially physically separate said receiving chamber and said contacting chamber from each other so as to preclude the return of oxygenated carrier liquid from said contacting chamber to said receiving chamber;
 - an oxygen gas inlet for introducing said oxygen gas molecules at a gas pressure slightly above the ambient surrounding air pressure into said apparatus, said oxygen gas inlet terminating in an end portion having a gas introduction orifice therein, said gas introduction orifice located in said receiving chamber, said gas introduction orifice being adapted to cause a jet of oxygen gas molecules to be emitted therefrom;.

a spray orifice located in said separating partition, said spray orifice being constructed and adapted to allow earlier liquid to be sprayed therethrough into said contacting chamber by said jet of oxygen gas molecules;

a passageway having a first end and a second end in fluid communication with each other, said first end located within said receiving chamber in fluid communication with said carrier liquid and said second end attached to said spray orifice to form a space between said gas introduction orifice and said spray orifice, such that said earlier liquid can pass from said receiving chamber to the space between said gas introduction orifice and said spray orifice into the receiving chamber; and an oxygenated earlier liquid outlet for allowing said oxygenated carrier liquid to exit from said contacting chamber;

wherein said oxygen gas molecules include molecules in the diatomic form ($O_2$), and molecules in at least one of either the triatomic form ($O_3$) and the monatomic form ($^1O_2$); and whereby, when said oxygen gas molecules are introduced into said apparatus through said oxygen gas inlet, said oxygen gas molecules exit said oxygen gas inlet through said gas introduction orifice so as to force the carrier liquid that is located in said space between said gas introduction orifice and said spray orifice to be sprayed through said spray orifice into said contacting chamber in a manner such that no bubbles are formed by said spray, thus causing said oxygen gas molecules to thoroughly contact said carrier liquid so as to thereby oxygenate said carrier liquid.

2. The oxygenation apparatus of claim 1, where said passageway is oriented such that said first end is lower than said second end.

3. The oxygenation apparatus of claim 2, wherein said passageway is substantially vertically oriented.

4. The oxygenation apparatus of claim 1, wherein said gas introduction orifice has a smaller diameter than said spray orifice.

5. The oxygenation apparatus of claim 1, wherein said contacting chamber comprises a top portion constructed and adapted to receive said spray of carrier liquid impacting thereagainst so as to cause increased contact of said oxygen gas molecules and said carrier liquid.

6. The oxygenation apparatus of claim 5, wherein said top portion is generally concave in shape.

7. The oxygenation apparatus of claim 1, wherein said contacting chamber has a generally sloped bottom surface constructed and adapted to allow said oxygenated carrier liquid to flow toward an outlet in said contacting chamber.

8. The oxygenation apparatus of claim 1, wherein said spray orifice is located substantially above said separating partition so as to keep any volume of said oxygenated carrier liquid on said separating partition below the level of said spray orifice.

9. The oxygenation apparatus of claim 1, wherein said gas introduction orifice is about 0.5 mm in diameter.

10. The oxygenation apparatus of claim 1, wherein said spray orifice is about 1.0 mm in diameter.

11. The oxygenation apparatus of claim 1, further comprising a one-way oxygen gas vent in said oxygenated carrier liquid outlet for precluding the back flow of fluids therepast.

* * * * *